(12) United States Patent
Tsukigi et al.

(10) Patent No.: US 9,933,306 B2
(45) Date of Patent: Apr. 3, 2018

(54) PHOTOELECTRIC SWITCH HAVING A CONTROLLER FOR CONTROLLING A LIGHT PROJECTING AMOUNT AND GENERATING A DETECTION SIGNAL REPRESENTING A WORKPIECE DETERMINATION

(71) Applicant: Keyence Corporation, Osaka (JP)

(72) Inventors: Shinichi Tsukigi, Osaka (JP); Sohei Kanoda, Osaka (JP); Yu Babasaki, Osaka (JP)

(73) Assignee: Keyence Corporation, Osaka (JP)

( * ) Notice: Subject to any disclaimer, the term of this patent is extended or adjusted under 35 U.S.C. 154(b) by 28 days.

(21) Appl. No.: 15/257,940

(22) Filed: Sep. 7, 2016

(65) Prior Publication Data

US 2017/0102266 A1 Apr. 13, 2017

(30) Foreign Application Priority Data

Oct. 8, 2015 (JP) .................. 2015-200557

(51) Int. Cl.
*G01J 3/02* (2006.01)
*G01J 3/28* (2006.01)
(Continued)

(52) U.S. Cl.
CPC .......... *G01J 3/0275* (2013.01); *B23K 26/032* (2013.01); *G01J 3/0208* (2013.01); *G01J 3/0237* (2013.01); *G01J 3/0262* (2013.01); *G01J 3/0286* (2013.01); *G01J 3/0289* (2013.01); *G01J 3/28* (2013.01); *G01J 3/36* (2013.01); *G01J 3/513* (2013.01); *G01N 21/251* (2013.01); *G01N 21/31* (2013.01); *G01V 8/12* (2013.01); *G05B 19/401* (2013.01);
(Continued)

(58) Field of Classification Search
CPC .......... G01J 3/0275; G01J 3/0286; G01J 3/28; G01N 21/251; G01N 21/31; G05B 19/401
USPC ................................ 250/205, 239, 216, 221
See application file for complete search history.

(56) References Cited

U.S. PATENT DOCUMENTS 5,029,245 A * 7/1991 Keranen ................... G01J 1/08
250/205
6,124,936 A 9/2000 Okamoto
(Continued)

FOREIGN PATENT DOCUMENTS

JP H11-330940 A 11/1999
JP 2005-127869 A 5/2005
(Continued)

*Primary Examiner* — Que T Le
(74) *Attorney, Agent, or Firm* — Kilyk & Bowersox, P.L.L.C.

(57) ABSTRACT

There is provided a photoelectric switch capable of reducing a size of a whole device while suppressing light amount irregularity and color irregularity of detected light. The photoelectric switch includes: a surface mount LED, configured to generate a light containing a plurality of color components with different hues; an optical shield disposed between the surface mount LED and a light projecting lens to shield the light around an optical opening passing the light from the surface mount LED to the light projecting lens; a light receiving element configured to selectively receive the light to generate a plurality of light reception signals; a controller configured to control a light projecting amount of the surface mount LED based on the light reception signal.

9 Claims, 10 Drawing Sheets

(51) Int. Cl.
| | |
|---|---|
| *G01V 8/12* | (2006.01) |
| *G01J 3/51* | (2006.01) |
| *B23K 26/03* | (2006.01) |
| *G01J 3/36* | (2006.01) |
| *G01N 21/31* | (2006.01) |
| *G05B 19/401* | (2006.01) |
| *G05B 19/404* | (2006.01) |
| *G01N 21/25* | (2006.01) |
| G01J 3/12 | (2006.01) |
| G01J 3/46 | (2006.01) |

(52) U.S. Cl.
CPC .... *G05B 19/404* (2013.01); *G01J 2003/1213* (2013.01); *G01J 2003/2833* (2013.01); *G01J 2003/466* (2013.01); *G01N 2201/062* (2013.01)

(56) References Cited

U.S. PATENT DOCUMENTS

| | | |
|---|---|---|
| 6,323,481 B2 | 11/2001 | Ueki |
| 6,392,214 B1 | 5/2002 | Okamoto |
| 7,098,441 B2 | 8/2006 | Yamaguchi et al. |
| 2015/0108376 A1 | 4/2015 | Kawaguchi |
| 2017/0102271 A1 | 4/2017 | Tsukigi |
| 2017/0171935 A1 | 6/2017 | Inubushi et al. |

FOREIGN PATENT DOCUMENTS

| | | |
|---|---|---|
| JP | 2005-134363 A | 5/2005 |
| JP | 2005-291748 A | 10/2005 |
| JP | 2008-175743 A | 7/2008 |

\* cited by examiner

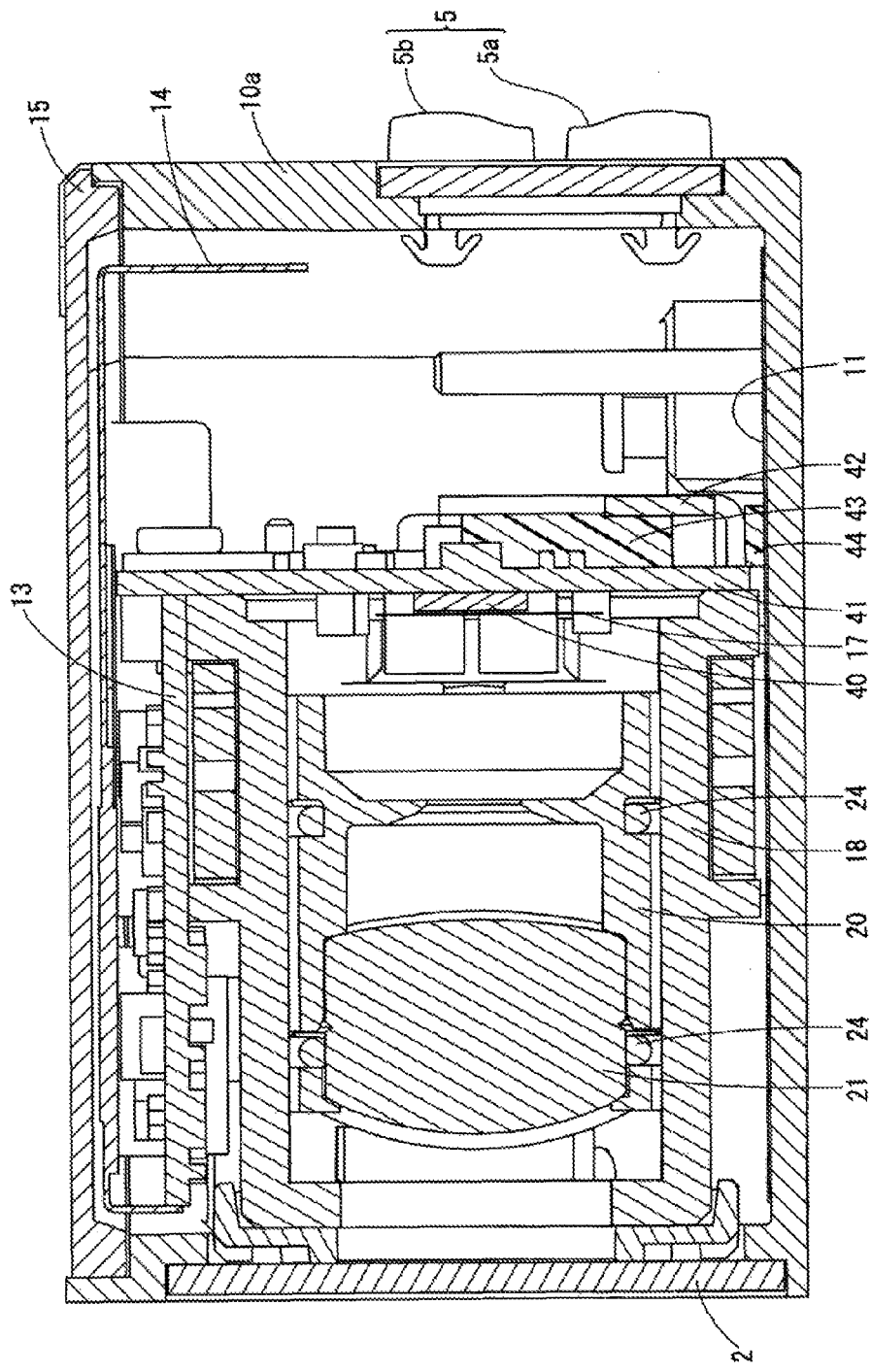
FIG. 2  A-A SECTIONAL VIEW

PHOTOELECTRIC SWITCH HAVING A CONTROLLER FOR CONTROLLING A LIGHT PROJECTING AMOUNT AND GENERATING A DETECTION SIGNAL REPRESENTING A WORKPIECE DETERMINATION

CROSS-REFERENCE TO RELATED APPLICATIONS

The present application claims foreign priority based on Japanese Patent Application No. 2015-200557, filed Oct. 8, 2015, the contents of which is incorporated herein by reference.

BACKGROUND OF THE INVENTION

1. Field of the Invention

The present invention relates to a photoelectric switch, and more specifically relates to improvement in photoelectric switch that receives reflected light from a detection area to acquire color information and performs workpiece determination.

2. Description of Related Art

A photoelectric switch is a detector for detecting a workpiece by use of light. The photoelectric switch projects detected light, and receives light reflected by or light transmitted through a workpiece, or some other light, to perform workpiece determination. Based on the result of the workpiece determination, the photoelectric switch generates a detection signal. Types of the photoelectric switch include: a light receiving amount-type photoelectric switch that performs workpiece determination by use of a light receiving amount of reflected light or transmitted light from a detection area including a workpiece; a distance measurement-type photoelectric switch that measures a distance to the workpiece to perform workpiece determination, and a color discrimination-type photoelectric switch that performs workpiece determination by discriminating colors of the workpiece surface.

The light receiving amount-type photoelectric switch performs workpiece discrimination through use of variation in light receiving amount due to a difference in reflectance or color of the workpiece surface, a difference in distance to the workpiece, a difference in tilt (tilt angle) of the workpiece surface, or the like. This is a general-purpose photoelectric switch applicable to a large number of uses.

Meanwhile, the distance measurement-type photoelectric switch measures a characteristic in accordance with the shape of the workpiece as a distance to the workpiece, to perform the workpiece determination. This is less susceptible to variation in reflectance and color of the workpiece surface or variation in tilt (tilt angle) of the workpiece surface. Further, the color discrimination-type photoelectric switch performs the workpiece determination by use of the color of the workpiece surface. This is less susceptible to variation in reflectance of the workpiece surface, variation in distance to the workpiece, or variation in tilt (tilt angle) of the workpiece surface.

A conventional color discrimination-type photoelectric switch includes: three light emitting elements for respectively generating red, green, and blue detected light; one light receiving element for receiving reflected light to generate a light reception signal; and an optical fiber cable for leading the detected light to a light projecting position (e.g., Unexamined Japanese Patent Publication No. 2005-134363 and Unexamined Japanese Patent Publication No. H11-330940). The three light emitting elements each have a structure where a light emitting diode is mounted in a cup integrally formed with a lead frame, and its periphery is molded into a shell shape by epoxy resin or the like. The photoelectric switch further includes: a wavelength selection-type dichroic mirror for aligning light, emitted from each light emitting element, to the same axis; and a condensing lens for concentrating light, aligned to the same axis, onto an optical fiber cable. In this photoelectric switch, colors of a workpiece is discriminated based on light receiving amount levels of the three colors obtained by sequentially lighting the respective light emitting elements in a time-division manner. Further, the detected light emitted from the light emitting element is transmitted through the optical fiber cable to obtain a light projection spot with reduced light amount irregularity.

In the conventional photoelectric switch described above, due to the need for using the optical fiber cable so as to reduce the light amount irregularity (color irregularity) of the detected light, it has been difficult to reduce a size of a whole detector even if the head portion can be reduced in size. When the light amount irregularity of the detected light is large, the accuracy deteriorates in color discrimination of a workpiece smaller than a light projection spot. Further, an optical system of the photoelectric switch described above needs to include three shell-type light emitting elements, two wavelength selection-type dichroic mirrors, and one condensing lens, and the optical system thus has a large size. Hence it has been difficult to reduce the size of the whole detector.

Moreover, the optical system of the photoelectric switch described above has an advantage in heat dissipation properties due to the light emitting elements being divided into three parts. However, since it is a shell-type light emitting element, if a drive current is increased so as to obtain high light projection intensity, the problem of the heat dissipation might become apparent, and it has thus been difficult to achieve both the high light projection intensity and the size reduction. Furthermore, in the foregoing photoelectric switch, in order to make a light emission intensity ratio with respect to the three light emitting elements constant, the light emission intensity of each light emitting element is detected by a monitor PD to control the light projection intensity so as to make light emission intensity for each light emitting element constant. There has thus been a problem of a small dynamic range for detection.

SUMMARY OF THE INVENTION

The present invention has been made in view of the above circumstances. It is an object of the present invention to provide a photoelectric switch capable of reducing a size of a whole device while suppressing light amount irregularity and color irregularity of detected light. Further, it is an object to provide a photoelectric switch capable of reducing a size of a whole device while ensuring high light projection intensity. Moreover, it is an object to provide a photoelectric switch capable of widening a dynamic range for detection.

A photoelectric switch according to one embodiment of the invention includes: a light emitting diode that is mounted on the surface of a circuit board and generates detected light containing two or more color components with different hues; a slit having an opening that is smaller than a light emitting surface of the light emitting diode, and disposed such that the opening faces the light emitting surface; a light projecting lens for concentrating the detected light, having passed through the opening, in the detection area; a light receiving element for selectively receiving reflected light from the detection area in association with two or more specific wavelengths, to generate two or more light reception signals respectively corresponding to light receiving amounts of the respective specific wavelengths; a light receiving lens for concentrating the reflected light from the detection area on the light receiving surface of the light receiving element; a light projecting amount controlling unit for controlling the light projecting amount of the light emitting diode based on the light reception signals; a color information acquiring unit for acquiring color information based on the two or more light reception signals respectively corresponding to the specific wavelengths; a coincidence degree calculating unit for comparing the acquired color information with color information of a reference color to calculate a coincidence degree of both of the color information; and a detection signal generating unit for comparing the coincidence degree with a previously defined determination threshold to perform workpiece determination, and generating a detection signal based on the result of the workpiece determination.

This photoelectric switch is a color discrimination-type photoelectric switch. By use of the light emitting diode for generating detected light containing two or more color components with different hues as the light source for light projection, light amount irregularity and color irregularity of detected light are reduced. Hence it is possible to reduce a size of a whole device while suppressing the light amount irregularity and the color irregularity of the detected light. Further, since the light emitting diode mounted on the surface of the circuit board has favorable heat dissipation properties as compared with a shell-type light emitting element, it is possible to reduce the size of the device while ensuring high light projection intensity. Moreover, since the high light projection intensity is ensured and the light projecting amount of the light emitting diode is controlled based on the light reception signal obtained by receiving the reflected light from the detection area, it is possible to widen the dynamic range for detection.

In addition to the above configuration, a photoelectric switch according to another embodiment of the invention includes: a metal heat sink disposed facing the rear surface of the circuit board; and a platy spacer that is made of thermally conductive resin, and in contact with the rear surface of the circuit board and the front surface of the heat sink. It is configured such that the spacer is disposed so as to overlap with the light emitting surface of the light emitting diode seen from a direction intersecting with the circuit board.

With such a configuration, the heat generated in the light emitting diode is transmitted from the circuit board to the heat sink via the spacer, and released through use of a space between the circuit board and the heat sink or a space of the rear surface of the heat sink, thereby allowing improvement in heat dissipation properties. In particular, since the spacer is disposed so as to overlap with the light emitting surface of the light emitting diode, the heat generated in the light emitting diode is effectively conducted to the heat sink.

In addition to the above configurations, a photoelectric switch according to still another embodiment of the invention includes a casing that is made of a thermally conductive material and accommodates the light emitting diode, the slit, the light projecting lens, the light receiving element, and the light receiving lens; and a block-like thermally conductive member made of thermally conductive resin. It is configured such that the thermally conductive member is disposed between a side wall of the casing and a bent section of the heat sink. With such a configuration, the heat generated in the light emitting diode is transmitted from the circuit board to the heat sink via the spacer and conducted to the casing via the thermally conductive member, thereby allowing further improvement in heat dissipation properties.

In addition to the above configurations, a photoelectric switch according to still another embodiment of the invention includes a sheet-like shield member having thermal conductivity and insulating properties, and disposed along the side wall. With such a configuration, the internal space of the casing can be electrically or magnetically shielded without preventing conduction of the heat from the circuit board and the heat sink to the casing. For example, when static electricity is added to the casing, in the inner space of the housing, damage of the circuit element such as the light emitting diode due to discharge can be prevented.

In addition to the above configurations, a photoelectric switch according to still another embodiment of the invention includes a display unit for displaying the coincidence degree on a display panel provided on the rear surface of the casing. With such a configuration, it is possible to easily confirm the coincidence degree according to the workpiece determination.

In addition to the above configurations, the photoelectric switch according to still another embodiment of the invention includes a determination threshold specifying unit for specifying the determination threshold based on press operation performed on an operation key provided on the rear surface of the casing. It is configured such that the display unit displays the determination threshold on the display panel. With such a configuration, it is possible to arbitrarily specify a determination threshold according to the workpiece determination, or change a previously defined determination threshold.

In addition to the above configurations, a photoelectric switch according to still another embodiment of the invention includes a light projection spot adjusting unit for operating an adjustment screw to adjust a distance to or a size of a light projection spot formed of the detected light. With such a configuration, it is possible to arbitrarily specify or change the distance to the light projection spot or the size of the light projection spot.

In addition to the above configurations, a photoelectric switch according to still another embodiment of the invention is configured such that the light projection spot adjusting unit is made up of a cam plate that has a long hole tilted against a rotation axis direction of the adjustment screw and moves in a direction of the rotation axis in conjunction with rotation of the adjustment screw, and a cam slider that has a slider section disposed in the long hole and moves in a direction of a light axis of the light projecting lens in conjunction with movement of the cam plate, and the cam slider moves the light projecting lens in the light axis direction by the slider section moving along the inner wall surface of the long hole. With such a configuration, by operating the adjustment screw, the light projecting lens moves in the light axis direction and the distance between the light emitting diode and the light projecting lens changes, and hence it is possible to adjust the distance to the light projection spot in the light axis direction or the size of the light projection spot.

In addition to the above configurations, a photoelectric switch according to still another embodiment of the invention is configured such that at least one of the light projecting lens and the light receiving lens is a chromatic aberration correcting lens, and made up of two or more optical lenses with mutually different dispersion powers. With such a configuration, the chromatic aberration of the detected light is corrected, thereby allowing clarification of a contour of the light projection spot formed in the detection area.

According to the present invention, a light emitting diode that generates detected light containing two or more color components with different hues is used as a light source for light projection, and it is thereby possible to provide a photoelectric switch capable of reducing a size of a whole device while suppressing light amount irregularity and color irregularity of detected light. Further, a light emitting diode mounted on the surface of a circuit board is used as the light source for light projection, and hence it is possible to provide a photoelectric switch capable of reducing the size of the device while ensuring high light projection intensity. Moreover, while the high light projection intensity is ensured, a light projecting amount of the light emitting diode is controlled based on a light reception signal obtained by receiving reflected light from the detection area, and hence it is possible to provide a photoelectric switch with a wide dynamic range for detection.

BRIEF DESCRIPTION OF THE DRAWINGS

FIG. 2 is a sectional view showing a cross section in the case of cutting off the photoelectric switch of FIGS. 1A and 1B along a cutting line A-A;

DETAILED DESCRIPTION OF PREFERRED EMBODIMENT

Hereinafter, an embodiment of the present invention will be described with reference to the drawings. In the present specification, a description will be given taking a direction of a light axis (main axis) of a light projecting lens as a longitudinal direction for the sake of convenience. However, this does not restrict the position of the photoelectric switch according to the present invention when used.

<Photoelectric Switch 1>

Figure 1A:
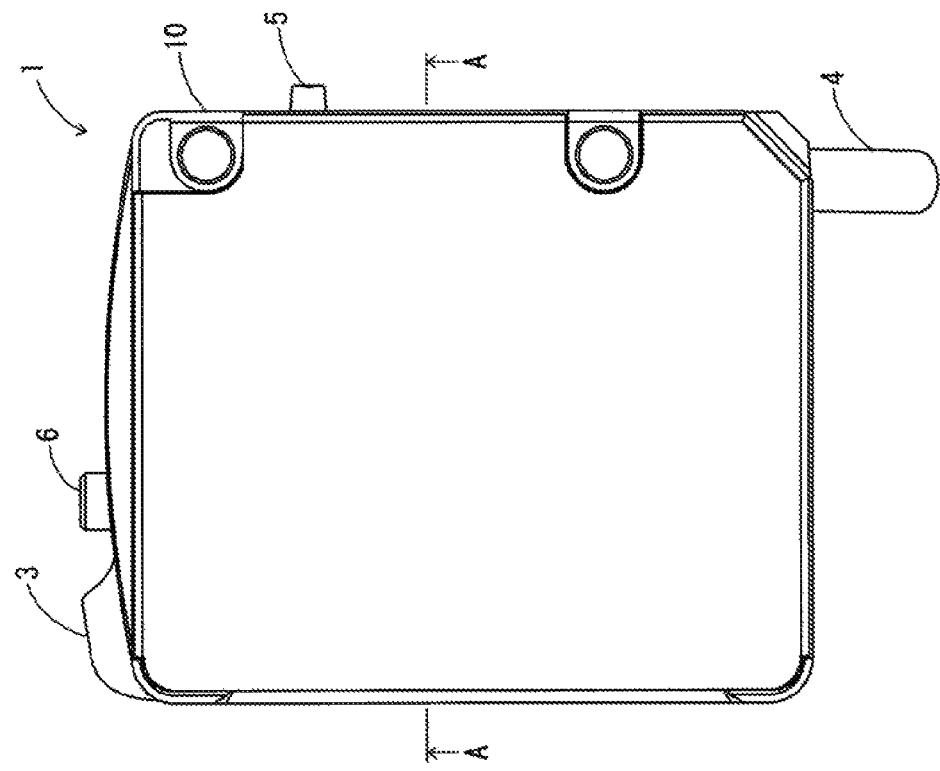
FIGS. 1A and 1B are plan views showing one configuration example of a photoelectric switch according to an embodiment of the present invention.
Figure 1B:
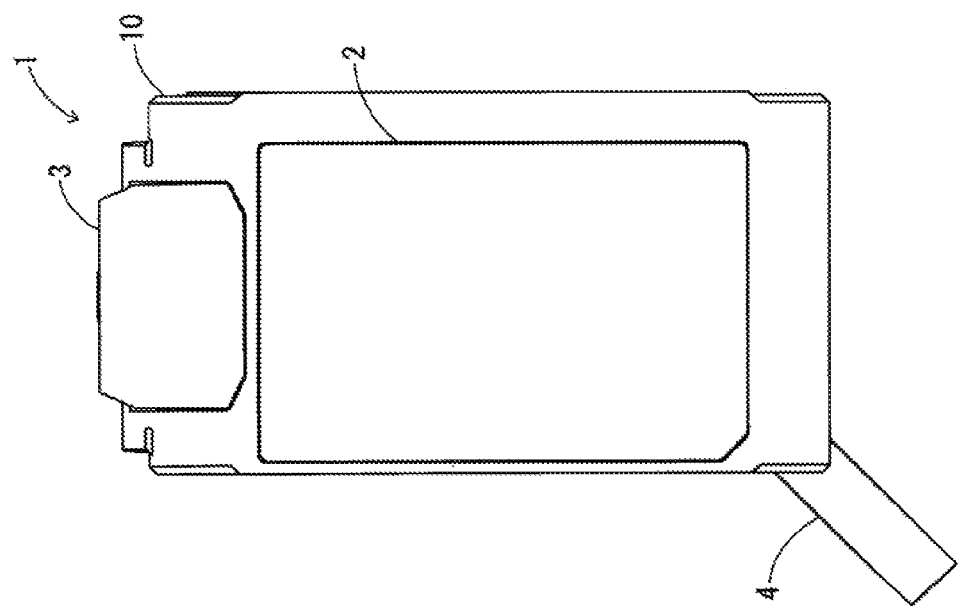
Figure 3:
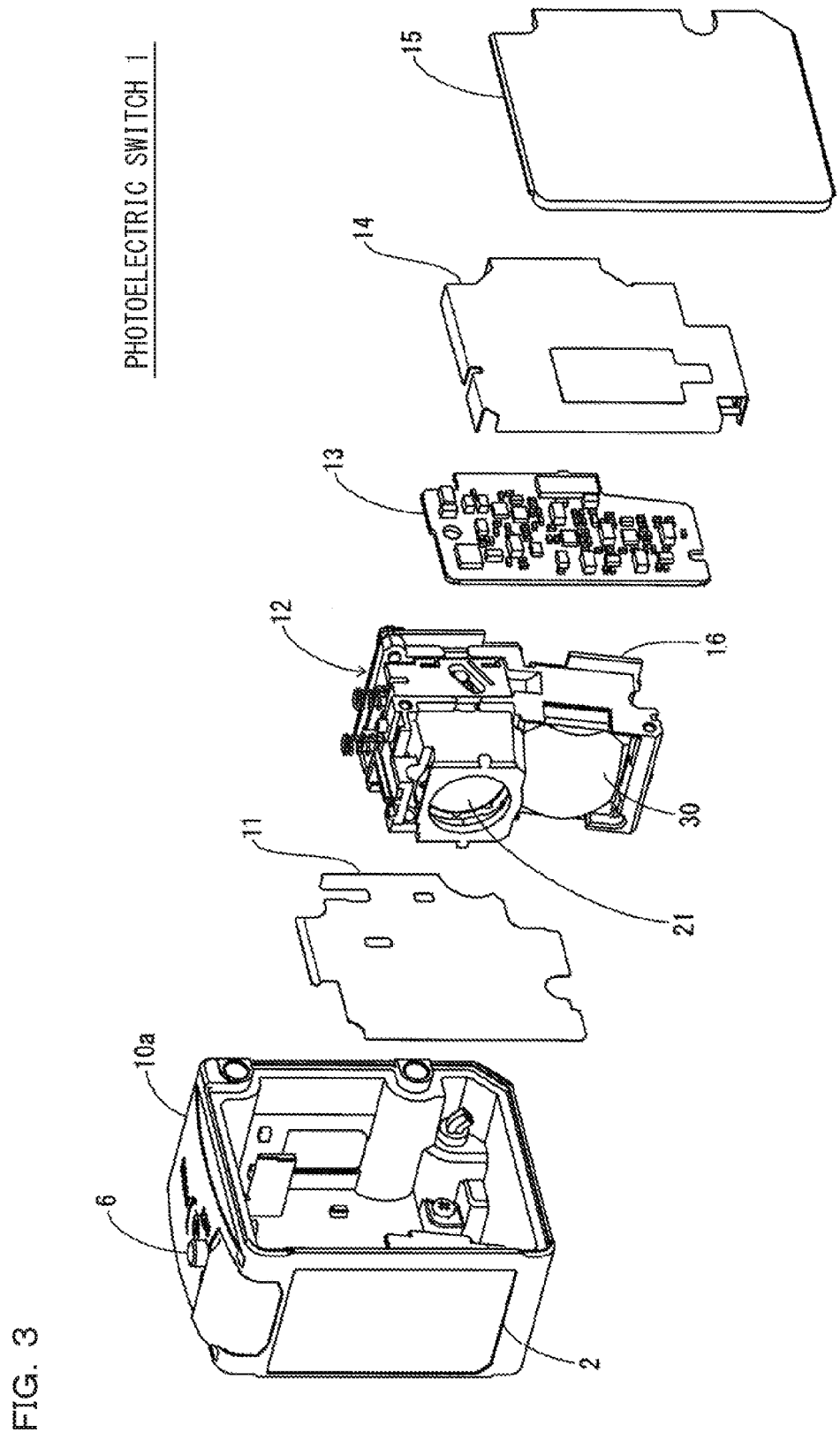
FIG. 3 is a perspective view showing the photoelectric switch of FIGS. 1A and 1B in a developed fashion.
Figure 4:
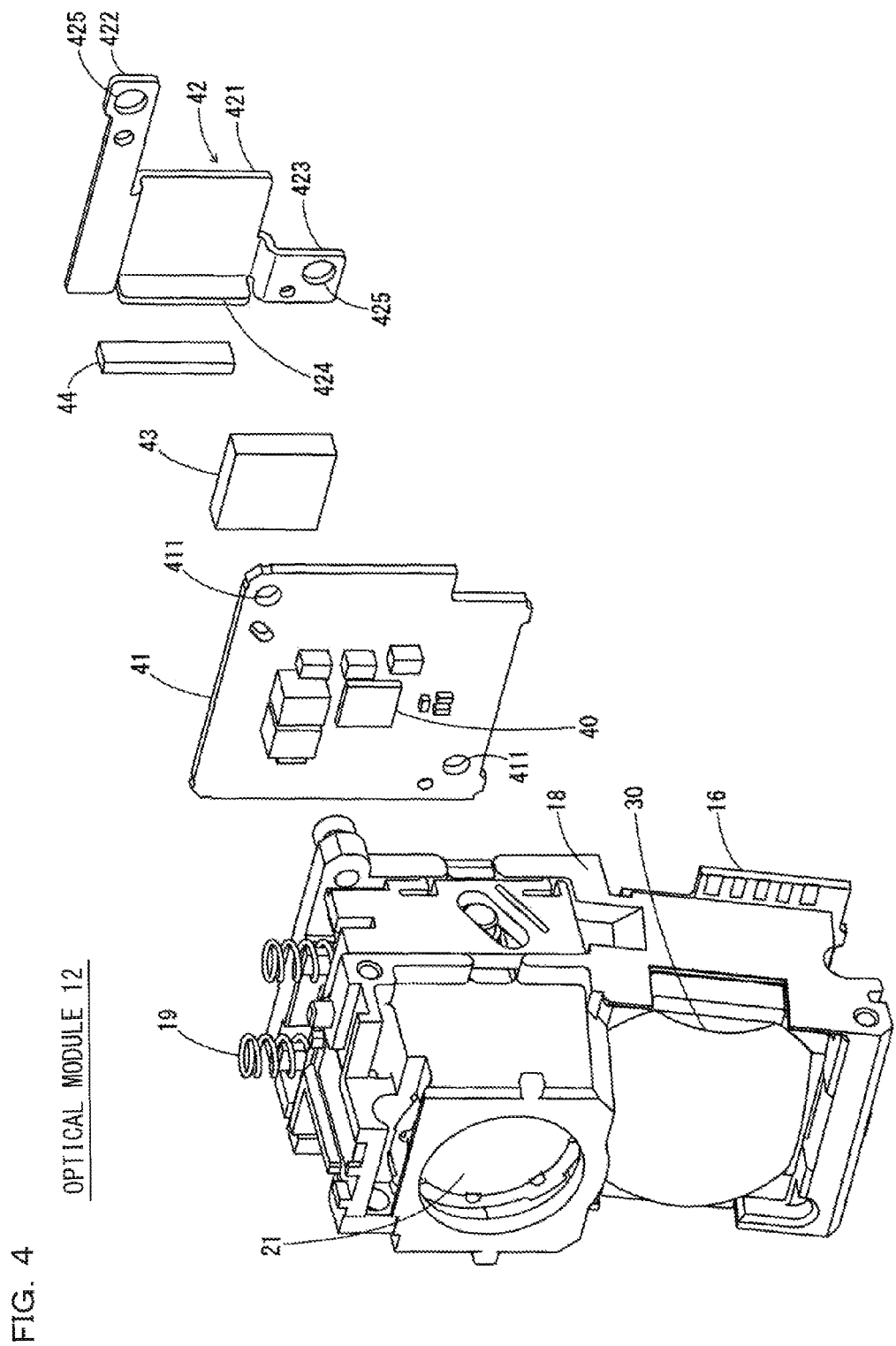
FIG. 4 is a perspective view showing an optical module of FIG. 3 in a developed fashion.

FIGS. 1A and 1B are plan views showing one configuration example of a photoelectric switch 1 according to an embodiment of the present invention, and shows a color discrimination-type photoelectric switch 1. FIG. 1A shows the front surface of a casing 10, and FIG. 1B shows the right lateral surface of the casing 10. FIG. 2 is a sectional view showing a cross section in the case of cutting off the photoelectric switch 1 of FIGS. 1A and 1B along a cutting line A-A. The figure shows the case of the cross section seen from a direction of an arrow. FIG. 3 is a perspective view showing the photoelectric switch 1 of FIGS. 1A and 1B in a developed fashion. FIG. 4 is a perspective view showing an optical module 12 of FIG. 3 in a developed fashion.

The photoelectric switch 1 is a detector that projects detected light and receives reflected light from a detection area to perform workpiece determination, and then outputs a detection signal based on the result of the workpiece determination. The workpiece determination is performed by discriminating colors of the workpiece surface, and the detection signal is outputted showing whether or not the workpiece is a desired one.

This photoelectric switch 1 is configured of a light projecting/receiving window cover 2, a workpiece determination indicator 3, a wire cable 4, operation keys 5, 6, a casing 10, an insulating film 11, an optical module 12, a main substrate 13, and a shield sheet 14.

The casing 10 is a casing for accommodating a circuit element and optical components, and is configured of a casing body 10a and a body cover 15. The casing body 10a is a box body with its right lateral surface opened. The body cover 15 is a shielding lid plate for shielding the opening of the casing body 10a, and fitted to the casing body 10a. The casing body 10a and the body cover 15 are formed of a thermally conductive material. The thermally conductive material is a material having thermal conductivity, and is excellent in heat dissipation properties.

For example, the casing body 10a and the body cover 15 are formed using, as the thermally conductive material, a metal which has a high thermal conductance rate as compared to that of resin or the like. In this photoelectric switch 1, a casing 10 made of zinc die-cast is used. Note that the casing 10 may be formed using, as the thermally conductive material, resin having its thermal conductance rate and strength improved by addition of a filler.

The detected light is emitted from the front surface of the casing 10, and the reflected light from the detection area is incident on the front surface. The light projecting/receiving window cover 2 is a transparent plate for protection which blocks an opening for light projection/reception formed on the front surface of the casing body 10a. The light projecting/receiving window cover 2 is fitted to the casing body 10a.

The workpiece determination indicator 3 and the operation key 6 are disposed on the upper surface of the casing 10. The workpiece determination indicator 3 is an indicator lamp which is lighted in accordance with the result of the workpiece determination, and is disposed at the front end of the upper surface of the casing. The operation key 6 is a press-type input button that is used at the time of specifying a reference color for workpiece determination.

The operation key 5 and a leader section of the wire cable 4 are disposed on the rear surface of the casing 10. The operation key 5 is a press-type input button that is used at the time of specifying a threshold for workpiece determination, and is configured of an up-key 5a and a down-key 5b. A numerical value can be incremented by operating the up-key 5a, and a numerical value can be decremented by operating the down-key 5b.

The wire cable 4 is configured of a power supply cable for supplying power to the circuit element in the casing 10, and a signal cable for transmitting a controlling signal and a detection signal. The leader section of the wire cable 4 is disposed at the lower end of the rear surface of the casing. This leader section is disposed at a corner formed of three surfaces, which are the rear surface, the bottom surface (lower surface), and the left lateral surface, of the casing 10.

The insulating film 11 has electric insulating properties, and is a sheet-like shield member disposed along the side wall of the casing body 10a. This insulating film 11 is a resin-made film electrically insulating the circuit element from the casing 10, and disposed so as to adhere to the left side wall.

While it is preferable that the insulating film 11 have high thermal conductivity, when the thickness of the film is lower than about 0.5 mm, the heat resistance is low enough without particularly considering the thermal conductivity. More preferably, when the thickness is about 0.1 mm, the heat can be dissipated to the casing 10 via the insulating film 11. Note that both the heat dissipation properties and the electric insulating properties can be achieved by interposing an insulating material with high thermal conductivity and insulating properties in place of the insulating film 11.

<Optical Module 12>

The optical module 12 is configured of a light receiving substrate 16, a slit 17, an optical base frame 18, a coil spring 19, a light projecting lens module 20, a light receiving lens 30, a light emitting diode 40, a light projecting substrate 41, a heat sink 42, a spacer 43, and a thermally conductive member 44. The optical base frame 18 is a support member that supports the optical components and the circuit board.

The light emitting diode 40 is a light emitting element that generates detected light containing two or more color components with different hues. This light emitting diode 40 is made of a rectangular semiconductor chip that generates white light as detected light, and mounted on the surface of the light projecting substrate 41. The light projecting substrate 41 is a circuit board provided with a circuit element for light projection such as the light emitting diode 40. This light projecting substrate 41 is fixed to the optical base frame 18, with the light emitting diode 40 facing forward.

The heat sink 42 is a heat sink member for dissipating the heat generated in the circuit element such as the light emitting diode 40, and is formed of a metal plate. For example, an aluminum-made heat sink 42 is used. This heat sink 42 is configured of an element facing section 421, substrate attachment sections 422, 423, and a side wall facing section 424. The heat sink 42 is disposed so as to face the rear surface of the light projecting substrate 41. Note that the heat sink 42 is not restricted to a metal plate so long as being a member with high thermal conductivity, and may be formed of thermally conductive resin, for example.

The element facing section 421 is formed in a position parallel to the light projecting substrate 41, and overlapping with the light emitting surface of the light emitting diode 40 seen from a direction intersecting with the light projecting substrate 41. The substrate attachment sections 422, 423 are both located closer to the front than the element facing section 421, and separately connected to the element facing section 421 via bent sections. The heat sink 42 is fixed to the light projecting substrate 41 by fitting the substrate attachment sections 422, 423 to the light projecting substrate 41. The light projecting substrate 41 is formed with through holes 411 in positions corresponding to fitting holes 425 that are formed in the substrate attachment sections 422, 423 of the heat sink 42. The heat sink 42 is fitted to the optical base frame 18, with the light projecting substrate 41 sandwiched therebetween and with the spacer 43 sandwiched between the heat sink 42 and the light projecting substrate 41, so that the heat sink 42 is fixed to the light projecting substrate 41 and the optical base frame 18. The side wall facing section 424 is a bent section parallel to the left side wall of the casing body 10a, and is connected to the element facing section 421.

The spacer 43 is a platy thermally conductive member which is made of thermally conductive resin having electric insulating properties and is in contact with the rear surface of the light projecting substrate 41 and the front surface of the heat sink 42. This spacer 43 is disposed between the element facing section 421 and the light projecting substrate 41, so as to overlap with the light emitting surface of the light emitting diode 40 seen from the direction intersecting with the light projecting substrate 41.

The spacer 43 is preferably formed of a member having high adhesive followability to the uneven surface and the bent surface, such as rubber, elastomer, or a gel-like body. The spacer 43 adheres to the rear surface of the light projecting substrate 41 and the front surface of the heat sink 42, to achieve high heat dissipation properties. For example, the spacer 43 is made of silicone rubber, acrylic resin rubber, elastomer, or a gel-like body, having electric insulating properties and thermal conductivity.

The thermally conductive member 44 is a block-like member made of thermally conductive resin, and disposed between the side wall of the casing body 10a and the side wall facing section 424 of the heat sink 42. This thermally conductive member 44 is made up a flat plate extending in a vertical direction. For example, the spacer 43 and the thermally conductive member 44 are formed of silicone rubber. When the heat sink 42 is made of metal, the thermally conductive member 44 preferably has electric insulating properties. When the insulating film 11 is not to be provided, the thermally conductive member 44 preferably has electric insulating properties.

The thermally conductive member 44 is preferably formed of a member having high adhesive followability to the uneven surface and the bent surface, such as rubber, elastomer, a gel-like body, or the like. The thermally conductive member 44 adheres to the insulating film 11 disposed on the side wall of the casing body 10a and to the side wall facing section 424 of the heat sink 42, to achieve high heat dissipation properties. For example, the thermally conductive member 44 is made of silicone rubber, acrylic resin rubber, elastomer, or a gel-like body, having electric insulating properties and thermal conductivity. When the insulating film 11 is not to be provided, the thermally conductive member 44 adheres to the side wall of the casing body 10a and the side wall facing section 424 of the heat sink 42.

The slit 17 is an optical element having an opening smaller than the light emitting surface of the light emitting diode 40, and disposed such that the opening faces the light emitting surface. This slit 17 is made up of a metal plate formed with one through hole, and the plate surface is subjected to blackening, or the plate surface is formed with a black coated film. The slit 17 preferably has the plate surface subjected to matte blackening, or the plate surface formed with a matte black coated film. In this slit 17, the opening is made up of a through hole. For example, the slit 17 is formed of stainless steel. The opening of the slit 17 has a circular or rectangular shape. The slit 17 is fixed to the optical base frame 18, The light projecting lens module 20 is an optical unit including the light projecting lens 21, and is fitted to the optical base frame 18 movably in the light axis direction. The light projecting lens 21 is an optical element that forms an image of the detected light, having passed through the opening of the slit 17, in the detection area.

The light receiving substrate 16 is a circuit board provided with a circuit element for light reception such as the light receiving element. The light receiving substrate 16 is fixed to the optical base frame 18 in a state where the light receiving surface of the light receiving element faces forward. The light receiving lens 30 is an optical element that forms an image of the reflected light, emitted from the detection area, on the light receiving surface. The optical components and the circuit element for light reception are disposed on the closer side to the bottom than the light projecting lens module 20.

The coil spring 19 is an energization member that energizes the optical base frame 18, or a light projection spot adjuster described later, downward with respect to the casing body 10a so as to prevent backlash. This coil spring 19 is disposed between the upper wall of the casing body 10a and the optical module 12.

The foregoing insulating film 11 is disposed between the casing body 10a and the optical module 12. The thermally conductive member 44 is disposed in contact with the insulating film 11 and the side wall facing section 424 of the heat sink 42.

The main substrate 13 is a circuit board provided with a circuit element such as an arithmetic circuit. This main substrate 13 is fitted to the optical base frame 18, with the circuit formation surface facing the body cover 15 side. Only one surface of the main substrate 13 may be the circuit formation surface, or both surfaces may each be the circuit formation surface. The shield sheet 14 is a sheet-like shield member having electrostatic, magnetic, or electromagnetic shielding performance. This shield sheet 14 is a sheet for insulating the circuit element in the casing 10 in an electrostatic, magnetic, or electromagnetic manner. The shield sheet 14 is disposed between the main substrate 13 and the body cover 15. The shield sheet 14 may be covered with a resin-made film having electric insulating properties.

Figure 5:
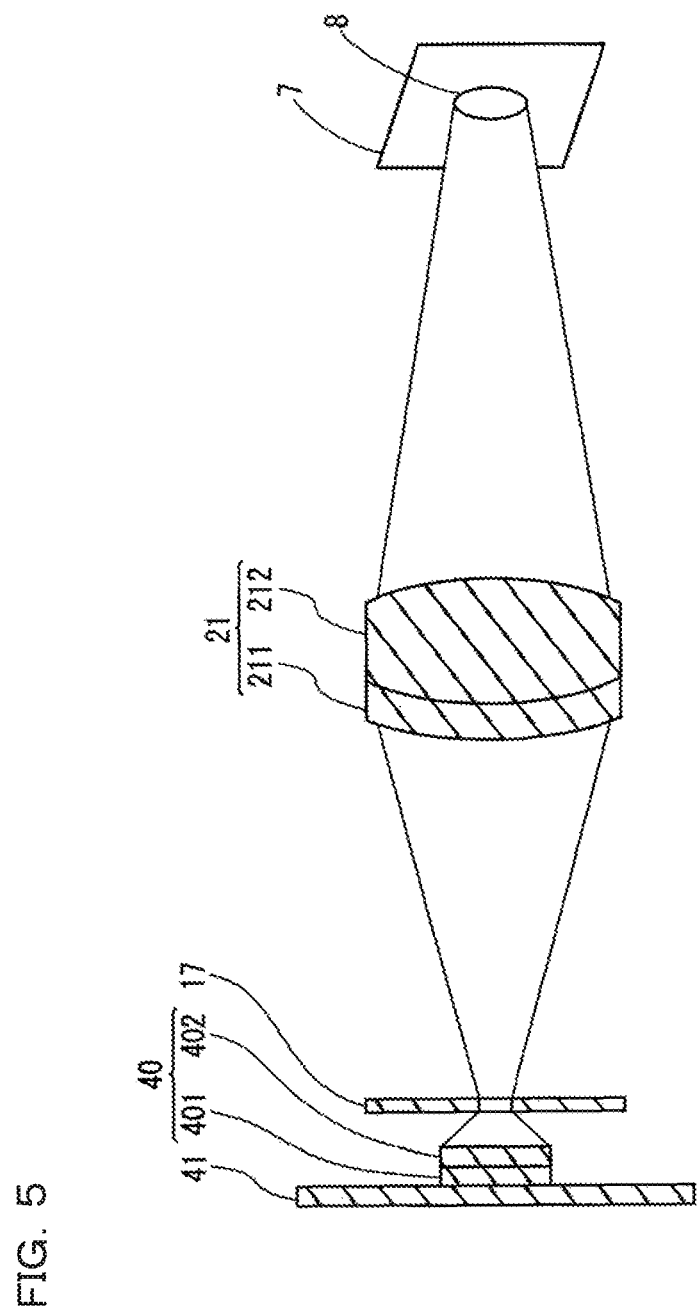
FIG. 5 is an explanatory view schematically showing an optical component for light projection.

FIG. 5 is an explanatory view schematically showing optical components for light projection, the figure showing the light emitting diode 40, the slit 17, and the light projecting lens 21. This light emitting diode 40 is a white LED (Light Emitting Diode) that mixes lights of two colors having a complementary relation to generate white light.

For example, the light emitting diode 40 is made up of a laminate formed by laminating a semiconductor element layer 401 for emitting blue light, and a fluorescent body layer 402 having a fluorescent body. In the fluorescent body layer 402, a fluorescent body is fixed by translucent resin or glass. The fluorescent body is excited by emitted light of the semiconductor element layer 401, and emits light such as yellow light, which has a longer wavelength than that of blue light.

The light projecting lens 21 is a chromatic aberration correcting lens for suppressing chromatic aberration, the lens being made up of two or more optical lenses with dispersion powers different from each other. For example, the light projecting lens 21 is an achromatic lens, and made up of two optical lenses, a high dispersion lens 211 and a low dispersion lens 212.

The high dispersion lens 211 is a concave lens with a high dispersion power. The low dispersion lens 212 is a convex lens with a low dispersion power. The high dispersion lens 211 is disposed on the closer side to the light emitting diode 40 than the low dispersion lens 212. Note that an apochromatic lens made up of three optical lenses may be used for the light projecting lens 21.

The slit 17 is disposed between the light emitting diode 40 and the light projecting lens 21. For example, the slit 17 is disposed in the vicinity of the light emitting diode 40 and around a focus of the light projecting lens 21. Specifically, the slit 17 is disposed in a distance of about 0.1 mm from the light emitting diode 40. A size of the light emitting surface of the light emitting diode 40 is about 1 mm, whereas a diameter of the opening of the slit 17 is 0.27 mm. A thickness of the slit 17 is about 0.1 mm.

Out of the detected light emitted from the light emitting surface of the light emitting diode 40, light from the periphery of the light emitting diode 40 is shielded by the slit 17. The detected light having passed through the opening of the slit 17 is subject to a refractive function by the light projecting lens 21, and an image of the light is formed in the detection area 7 as a light projection spot 8. The slit 17 on the light projection side does not reduce a light amount but forms an image in the slit section as the light projection spot 8, to thereby make the spot clear without light amount irregularity and color irregularity.

Further, employing the achromatic lens to the light projecting lens 21 leads to reduction in chromatic aberration. Hence it is possible to obtain the light projection spot 8 with a clear contour. By making the distance between the light emitting diode 40 and the light projecting lens 21 variable, the distance from the light projecting lens 21 to the detection area 7 can be changed within a range of 30 mm to 500 mm.

Note that the opening of the slit 17 may only be an opening that transmits part of the detected light emitted from the light emitting diode 40. For example, in place of the through hole, the opening may be a light transmitting window formed in a transparent glass plate.

<Light Projecting Lens Module 20>

Figure 6:
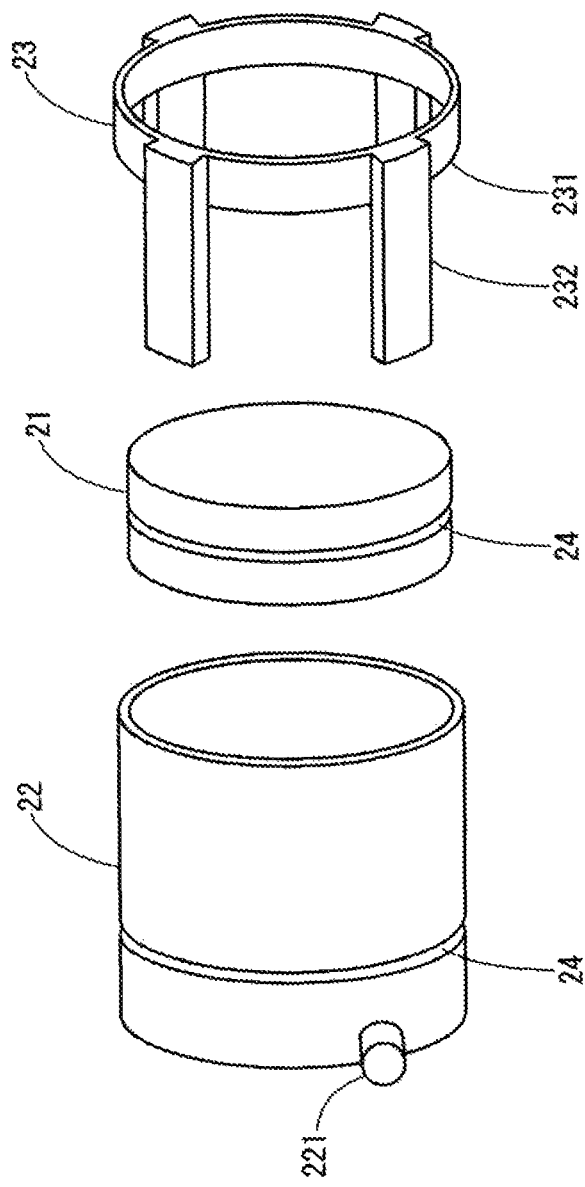
FIG. 6 is a perspective view showing a light projecting lens module in a developed fashion.

FIG. 6 is a perspective view showing the light projecting lens module 20 in a developed fashion. This light projecting lens module 20 is configured of a light projecting lens 21, a lens holder 22, a lens presser 23, and an O-ring 24. The lens holder 22 is a cylindrical holding member for holding the light projecting lens 21, and accommodates part of the light projecting lens 21.

This lens holder 22 functions as a cam slider of a light projection spot adjuster described later, and is provided with a slider section 221 to be engaged with a cam plate. The slider section 221 is a columnar projection projecting from the outer peripheral surface.

The lens presser 23 is configured of an annular ring section 231 that encloses part of the light projecting lens 21, and four hook sections 232 extending from the ring section 231 in the light axis direction of the light projecting lens 21. The light projecting lens 21 is fixed to the lens holder 22 by mounting the lens presser 23 onto the lens holder 22 where the light projecting lens 21 is accommodated.

The O-ring 24 is an annular sealing member, and disposed on the lens holder 22 and the light projecting lens 21. The O-ring 24 disposed on the outer peripheral surface of the lens holder 22 centers the lens holder 22 with respect to the optical base frame 18, and increases frictional resistance at the time of the lens holder 22 moving in the light axis direction. Further, the O-ring 24 disposed on the outer peripheral surface of the light projecting lens 21 centers the light projecting lens 21 with respect to the lens presser 23.

<Light Projection Spot Adjuster 50>

Figure 7A:
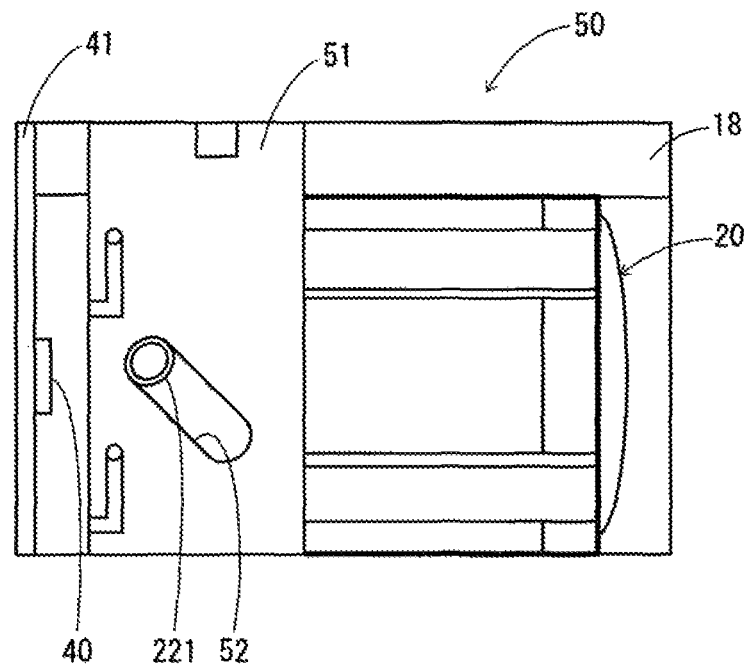
FIGS. 7A and 7B are plan views showing a configuration example of a light projection spot adjuster.
Figure 7B:
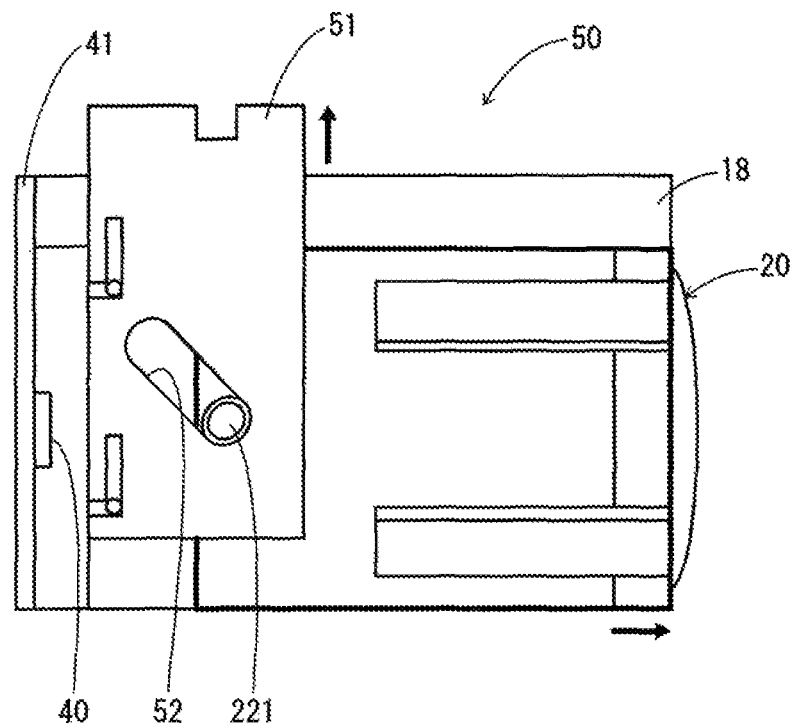

FIGS. 7A and 7B are plan views showing a configuration example of a light projection spot adjuster 50. FIG. 7A shows a case where the light projecting lens module 20 has been pulled to the rear surface side, and FIG. 7B shows a case where the light projecting lens module 20 has been pushed to the front surface side.

The light projecting lens module 20 is held by the optical base frame 18 movably in the light axis direction of the light projecting lens 21, namely in the longitudinal direction, and the movement of the light projecting lens module 20 in the vertical direction and a horizontal direction is limited. Specifically describing, the O-ring 24 disposed on the lens holder 22 of the light projecting lens module 20 is in contact with the optical base frame 18, thereby limiting the movement of the light projecting lens module 20 in the vertical direction and the horizontal direction, as well as increasing the frictional resistance in the light axis direction, to allow improvement in impact resistance.

The light projection spot adjuster 50 is configured of an adjustment screw described later, a cam plate 51 that moves in the vertical direction in conjunction with the rotation of the adjustment screw, and the lens holder 22 that functions as a cam slider. By operating the adjustment screw, the light projection spot adjuster 50 adjusts a distance or a size of the light projection spot 8 formed of the detected light. The light projection spot 8 is a slit image formed in the detection area 7. The distance to the light projection spot 8 in the light axis direction or the size (spot diameter) of the light projection spot 8 can be adjusted. The adjustment screw is rotated around the vertical rotation axis.

The cam plate 51 is made up of a metal plate having a long hole 52 tilted against the vertical direction. Two cam plates 51 are disposed on the right and left of the optical base frame 18 with the light projecting lens module 20 sandwiched therebetween.

The slider section 221 of the lens holder 22 is disposed in the long hole 52 of the cam plate 51. The lens holder 22 moves in the longitudinal direction in conjunction with the movement of the cam plate 51. That is, by turning the adjustment screw counterclockwise to press down the cam plate 51, the light projecting lens module 20 is pulled to the rear surface side. At this time, the image of the light projection spot 8 is formed nowhere and dispersed, and hence the diameter of the light projection spot 8 is the largest.

On the other hand, by turning the adjustment screw clockwise to pull up the cam plate 51, the light projecting lens module 20 is pushed out to the front surface side. At this time, the image formation position of the light projection spot 8 is the nearest position, and the diameter of the light projection spot 8 at the image formation position is also the smallest. For example, the farther the image formation position, the larger the diameter of the light projection spot 8. When the distance to the image formation position of the light projection spot 8 is 100 mm, a diameter $\Phi$ of the light projection spot 8 in the image formation position is: $\Phi=3.5$ mm. When the distance to the image formation position of the light projection spot 8 is 500 mm, a diameter $\Phi$ of the light projection spot 8 in the image formation position is: $\Phi=18$ mm. Note that the diameter of the light projection spot 8 at a position other than the image formation position of the light projection spot 8 is larger than the diameter of the light projection spot 8 in the image formation position. That is, the diameter of the light projection spot 8 can be arbitrarily adjusted by the adjustment screw.

Figure 8A:
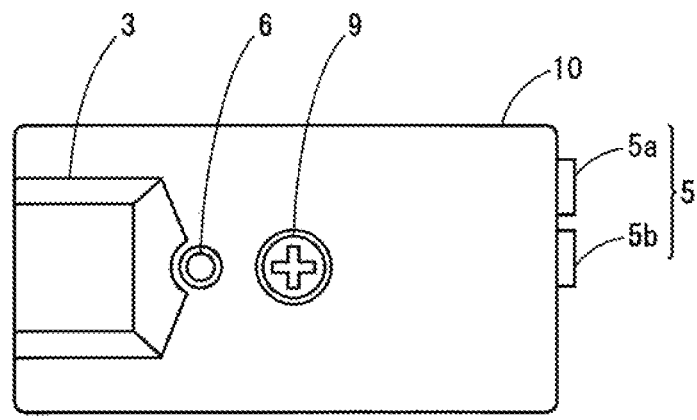
FIGS. 8A and 8B are plan views showing the upper surface and the rear surface of a casing.
Figure 8B:
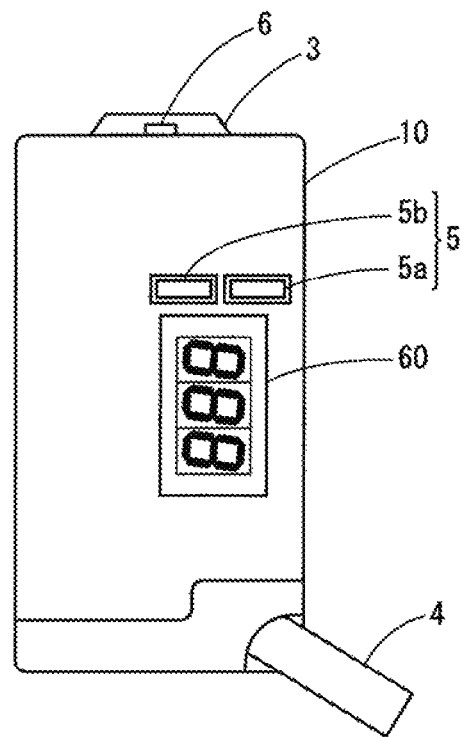

FIGS. 8A and 8B are plan views showing the upper surface and the rear surface of the casing 10. FIG. 8A shows the workpiece determination indicator 3, the operation key 6, and an adjustment screw 9 which are provided on the upper surface and FIG. 8B shows the operation key 5 and a display panel 60 which are provided on the rear surface.

The adjustment screw 9 is an operator constituting the light projection spot adjuster 50, and is used for adjusting the image formation position or the spot diameter of the light projection spot 8. By turning the adjustment screw 9 clockwise or counterclockwise around the vertical rotation axis, the cam plate 51 moves in the vertical direction, and the light projecting lens module 20 moves in the longitudinal direction. By operating the adjustment screw 9 in this manner, the distance to and the spot diameter of the light projection spot 8 can be changed even after installation of the photoelectric switch 1.

The display panel 60 is a display device for displaying a threshold for workpiece determination and a coincidence degree. For example, the display panel 60 is a seven-segment display. Note that an active matrix drive-type display device such as an LCD (liquid crystal display) may be used for the display panel 60.

Figure 9:
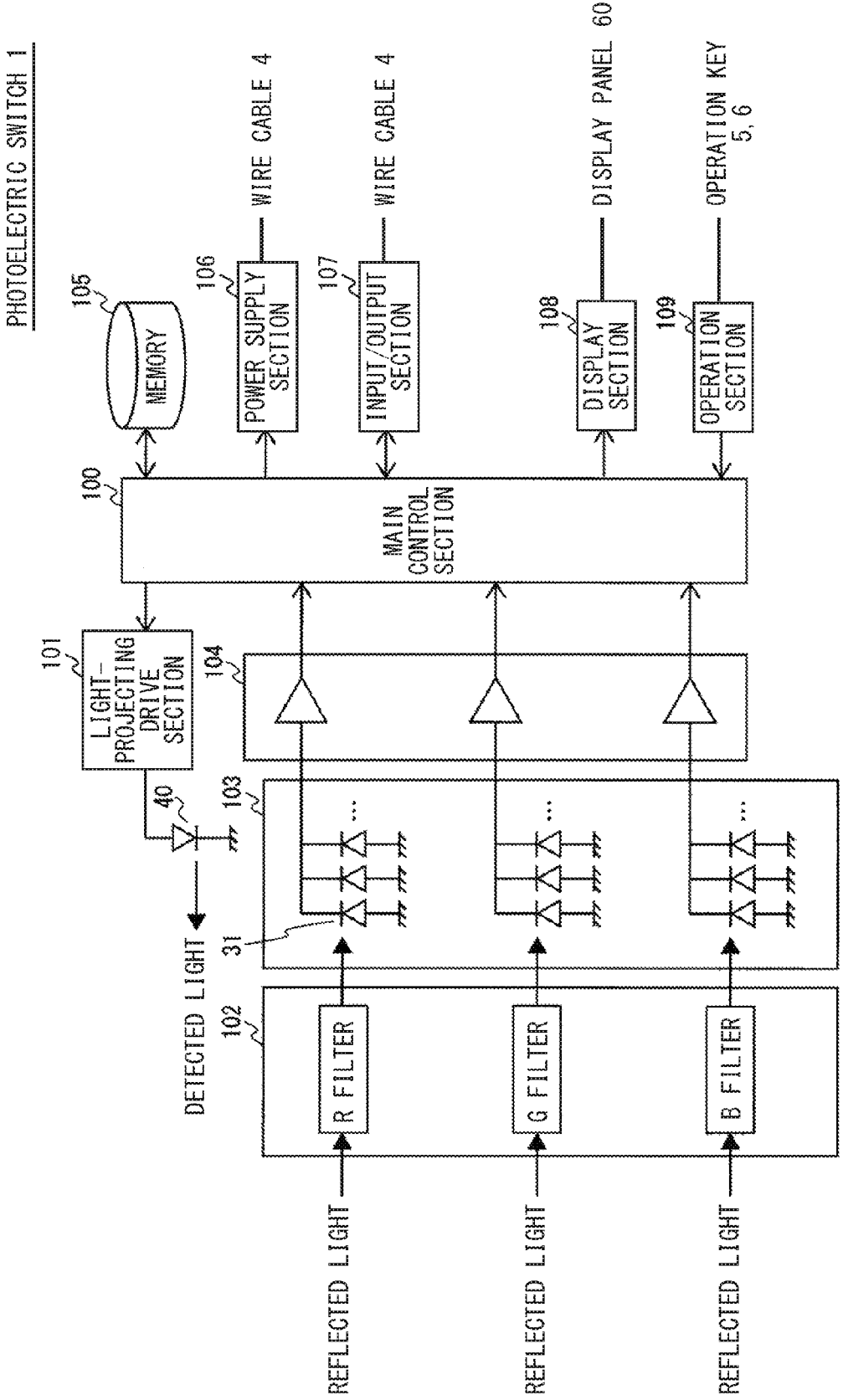
FIG. 9 is a block diagram showing one example of a functional configuration in the photoelectric switch of FIGS. 1A and 1B.

FIG. 9 is a block diagram showing one example of a functional configuration in the photoelectric switch 1 of FIGS. 1A and 1B. This photoelectric switch 1 is configured of a main control section 100, a light projection driving section 101, a color filter 102, a light receiving element 103, an amplification section 104, a memory 105, a power supply section 106, an input/output section 107, a display section 108, and an operation section 109.

The main control section 100 controls projected/received light, and performs the workpiece determination based on a light reception signal. The light projection driving section 101 drives the light emitting diode 40 based on instruction by the main control section 100. For example, the main control section 100 controls a light projecting amount to be instructed to the light projection driving section 101. The light projecting amount is controlled based on an amount of light received from the light receiving element 103 such that the light receiving amount is held within a certain range.

In the case of a workpiece with a high reflectance, since the light receiving amount is relatively large, the main control section 100 instructs a relatively small light projecting amount to the light projection driving section 101 based on the light receiving amount. On the other hand, in the case of a workpiece with a low reflectance, since the light receiving amount is relatively small, the main control section 100 instructs a relatively large light projecting amount to the light projection driving section 101 based on the light receiving amount. Further, the light projection driving section 101 pulse-drives the light emitting diode 40 based on instruction of the light projecting amount and instruction of the light projection timing by the main control section 100. When the light emitting diode 40 is to be pulse-driven, a pulse light emitting amount of the light emitting diode 40 may be measured by a monitor PD, not shown, and the light projection driving section 101 may be controlled such that the measured pulse light emitting amount is coincident with a predetermined target value. In this case, the main control section 100 can adjust the light emitting amount of the light emitting diode 40 by adjusting the target value.

The light receiving element 103 selectively receives the reflected light from the detection area 7 in association with two or more specific wavelengths, and generates two or more light reception signals respectively corresponding to light receiving amounts for the respective specific wavelengths. This light receiving element 103 is a multi-divisional PD unit where two or more PDs (Photo Diodes) 31 are two-dimensionally arrayed on the light receiving substrate 16. For example, the PDs 31 are arrayed in a 12×24-matrix form.

The color filter 102 is an optical element that selectively transmits light of a color component with a specific wavelength in accordance with a two-dimensional position, and is disposed on the light receiving surface of the light receiving element 103. In this color filter 102, an R filter area, a G filter area, and a B filter area, which respectively and selectively transmit red light, green light, and blue light, are arranged in a matrix form. Any of the R filter area, the G filter area, and the B filter area is made up of a minute rectangular area, and formed in association with the PD 31.

For example, in both the vertical direction and the horizontal direction, the B filter area, the G filter area, and the R filter area are disposed repeatedly in this order. Further, the same number of filter areas formed is the same for any of the R filter area, the G filter area, and the B filter area. The use of the color filter 102 as thus described enables each PD 31 of the light receiving element 103 to selectively receive red light, green light, or blue light.

Generally, when the distance to the workpiece changes, the position and the size of the image of the light projection spot 8 formed on the light receiving surface of the light receiving element 103 change. For this reason, when the division number of the color components is small, a signal ratio of RGB changes due to a variation in distance to the workpiece, making it difficult to accurately discriminate the color on the workpiece surface. In contrast, employing the foregoing multi-divisional PD unit as the light receiving element 103 can suppress a change in signal ratio of RGB, to thereby make the color discrimination less susceptible to the variation in distance.

On the other hand, when the division number of the color components is large, the change in the signal ratio due to the variation in distance is small, but a proportion of a partition formed between the PDs 31 is relatively larger, leading to an increase in light reception loss. Further, since the wiring to the PDs 31 increases, a parasitic capacitance increases, to cause deterioration in S/N ratio in an amplifier circuit. With consideration for these, when the filter is square, a preferable size of one filter area is that one side has a length of 50 μm to 200 μm. The shape of the filter is not restricted to square, but may be rectangular, another quadrangular, or hexagon. In this case, the area of the filter is preferably 2500 square μm to 40000 square μm.

Further, the larger the size of the image of the light projection spot 8 formed on the light receiving surface of the light receiving element 103, the smaller the change in RGB signal ratio when the distance to the workpiece is changed. Hence it is preferable to dispose the light receiving element 103 in a defocused position ahead of or behind the position of the image of the light projection spot 8 formed by the light receiving lens 30.

Meanwhile, when the image of the light projection spot 8 is in the state of running off the edge of the light receiving surface of the light receiving element 103, the light receiving amount is small, thus making it impossible to detect a workpiece with a low reflectance. With consideration for these, the distance between the light receiving lens 30 and the light receiving element 103 is adjusted such that the image of the light projection spot 8 includes not less than 50 filter areas.

The amplification section 104 is an amplifier unit that amplifies a light reception signal input from each PD 31 and outputs the amplified signal to the main control section 100. This amplification section 104 can switch a gain. The light reception signal is amplified for each color component with a specific wavelength and outputted to the main control section 100. The gain of the amplification section 104 is controlled by the main control section 100 such that the light receiving amount is held within a certain range based on a light reception signal representing a light receiving amount from the light receiving element 103 in a similar manner to adjustment of the light emitting amount of the light emitting diode 40 by the main control section 100. The main control section 100 may control both the gain of the amplification section 104 and the light emitting amount of the light emitting diode 40 based on the light reception signal.

The memory 105 holds a threshold for workpiece determination, color information of a reference color, and the like. The power supply section 106 is connected to external equipment such as a controller via the wire cable 4, and supplies a direct current to the main control section 100 and the light projection driving section 101 based on control of the main control section 100. The input/output section 107 is connected to the external equipment such as the controller via the wire cable 4. The input/output section 107 receives a controlling signal, outputs the received signal to the main control section 100, and transmits a detection signal input from the main control section 100 to the external equipment.

The display section 108 displays on the display panel 60 a threshold for workpiece determination and a coincidence degree based on control of the main control section 100. The operation section 109 generates an operation signal based on press operation on each of the operation keys 5, 6, and outputs the generated operation signal to the main control section 100.

<Main Control Section 100>

Figure 10:
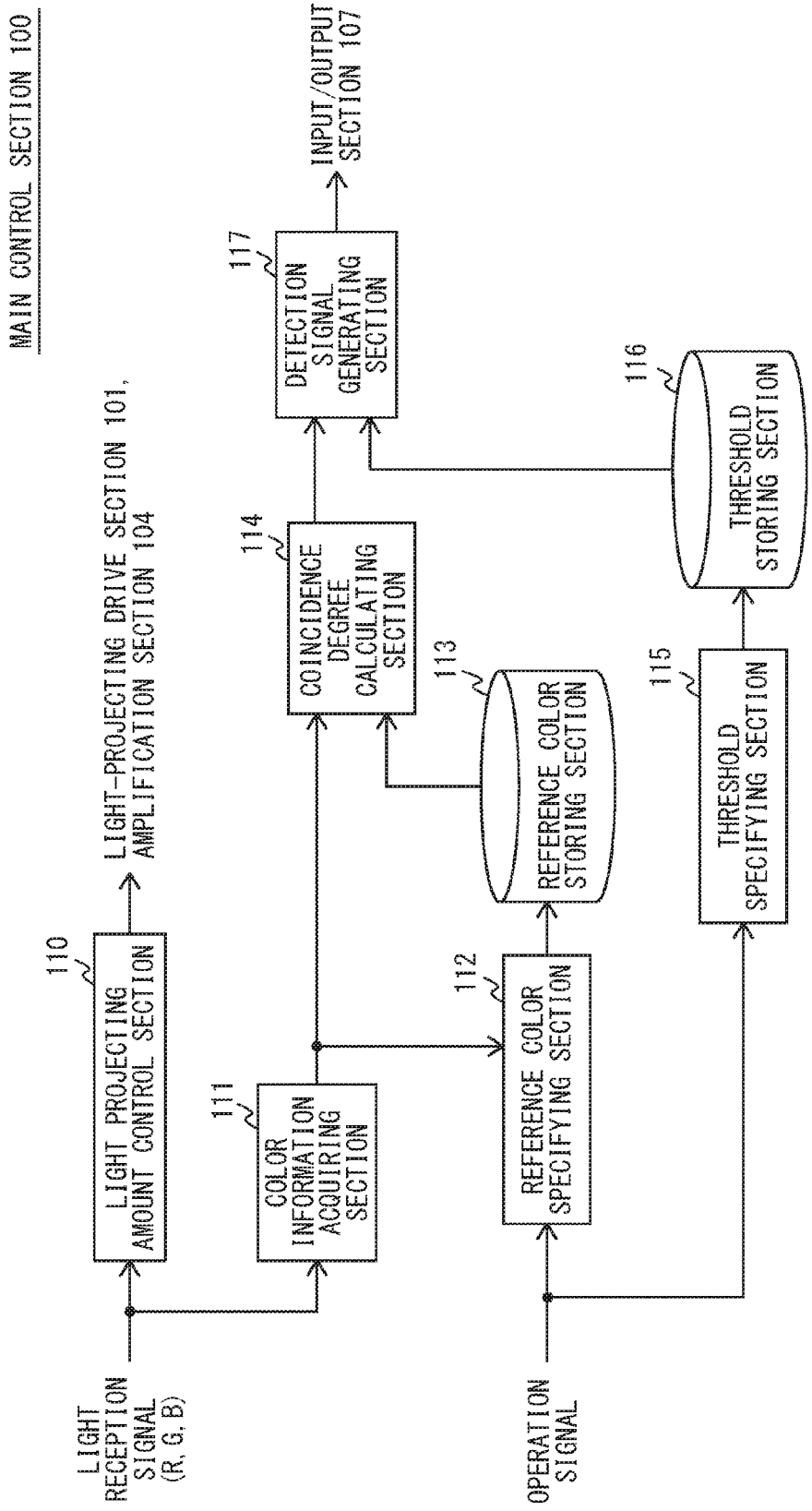
FIG. 10 is a block diagram showing a configuration example of a main control section of FIG. 9.

FIG. 10 is a block diagram showing a configuration example of the main control section 100 of FIG. 9. This main control section 100 is configured of a light projecting amount control section 110, a color information acquiring section 111, a reference color specifying section 112, a reference color storing section 113, a coincidence degree calculating section 114, a threshold specifying section 115, a threshold storing section 116, and a detection signal generating section 117.

Based on a light reception signal input from the amplification section 104, the light projecting amount control section 110 controls the light projection driving section 101 to adjust an amount of light projected by the light emitting diode 40. For example, in a case where the light receiving amount of the reflected light exceeds a certain level, the following control is performed: the light projecting amount is decreased, and when the light receiving amount falls below a certain level, the light projecting amount is increased to return to its original state.

In this light projecting amount control section 110, based on the light reception signal input from the amplification section 104, the amplification section 104 is controlled to switch a gain. For example, in a case where the light receiving amount of the reflected light exceeds a certain level, the following control is performed: the gain of the amplification section 104 is decreased, and when the light receiving amount of the reflected light falls below a certain level, the gain of the amplification section 104 is increased to return to its original state. The above control of the light projecting amount is performed based on a light receiving amount of any of RGB. Alternatively, it is performed based on a parameter obtained by combining each of the light receiving amounts of RGB.

The color information acquiring section 111 acquires color information based on two or more light reception signals corresponding to specific wavelengths, and outputs the acquired color information to the coincidence degree calculating section 114 and the reference color specifying section 112. The acquired color information is defined based on light receiving amount levels of the three colors. For example, when it is assumed that the light receiving amount level of red light is $R_1$, the light receiving amount level of green light is $G_1$, the light receiving amount level of blue light is $B_1$, and a sum of the light receiving amount is: $M_k = R_k + G_k + B_k$, a color is represented by a set $(r_1, g_1, b_1)$ by use of a ratio of the light receiving amount levels of the three colors: $r_k=R_k/M_k$, $g_k=G_k/M_k$, $b_k=B_k/M_k$.

Based on press operation performed on the operation key 6, the reference color specifying section 112 specifies color information ($r_0$, $g_0$, $b_0$) acquired by the color information acquiring section 111 as the color information of the reference color. The reference color storing section 113 then holds the color information ($r_0$, $g_0$, $b_0$) of the reference color registered by the reference color specifying section 112.

The coincidence degree calculating section 114 compares the color information($r_1$, $g_1$, $b_1$) acquired by the color information acquiring section 111 with the color information ($r_0$, $g_0$, $b_0$) of the reference color registered into the reference color storing section 113. Based on the result of the comparison, the coincidence degree calculating section 114 calculates a coincidence degree C. of both color information, and outputs it to the detection signal generating section 117. The coincidence degree C. is a one-dimensional parameter showing a coincidence degree of colors, and made up of a relative value of the current light receiving amount with respect to the light receiving amount of the reference color. With this coincidence degree C., quantitative evaluation is made as to how much a color to be compared is similar to the color registered as the reference for the workpiece determination.

For example, the coincidence degree C. is represented by an integer in a range not smaller than 0 and not larger than 999. When the color of the workpiece is completely coincident with the reference color, the coincidence degree C. is 999. The display section 108 displays on the display panel 60 the coincidence degree C. calculated by the coincidence degree calculating section 114. Although the set ($r_k$, $g_k$, $b_k$) of $r_k$, $g_k$, $b_k$ as the ratio of the light receiving amount levels of the respective colors has been exemplified as the color information, in the present invention, the configuration of the color information is not restricted to this example. For example, a set ($R_k$, $G_k$, $B_k$) of the light receiving amount level of the red light, the light receiving amount level of the green light, and the light receiving amount level of the blue light may be used as the color information. Further, the color information is not restricted to the RGB color system, but a set made up of values of respective color components based on a color system such as Lab may be taken as the color information.

The threshold specifying section 115 specifies a threshold for workpiece determination as the determination threshold based on the press operation performed on the operation key 5. The display section 108 displays on the display panel 60 a determination threshold specified by the threshold specifying section 115. The threshold storing section 116 then holds the determination threshold registered by the threshold specifying section 115.

The detection signal generating section 117 compares the coincidence degree C., calculated by the coincidence degree calculating section 114, with a determination threshold to perform the workpiece determination. Based on the result of the workpiece determination, the detection signal generating section 117 generates a detection signal and outputs it to the input/output section 107.

According to the present embodiment, by using the light emitting diode 40 for generating detected light containing two or more color components with different hues as the light source for light projection, the light amount irregularity and the color irregularity of the detected light can be reduced, and hence it is possible to reduce the size of the whole device while suppressing the light amount irregularity and the color irregularity of the detected light. Further, since the light emitting diode 40 mounted on the surface of the light projecting substrate 41 has favorable heat dissipation properties as compared with a shell-type light emitting element, it is possible to reduce the size of the device while ensuring high light projection intensity. Moreover, since the high light projection intensity is ensured and the light projecting amount of the light emitting diode 40 is controlled based on a light reception signal obtained by receiving reflected light from the detection area 7, it is possible to widen the dynamic range for detection.

Furthermore, since the chromatic aberration of the detected light is corrected by using the chromatic aberration correcting lens as the light projecting lens 21, it is possible to clarify a contour of the light projection spot 8 formed in the detection area 7.

In the present embodiment, the example of the case has been described where the achromatic lens is used for the light projecting lens 21. However, in the present invention, the configuration of the optical module 12 is not restricted to this example. For example, the optical module 12 may be configured using the chromatic aberration correcting lens such as the achromatic lens for the light receiving lens 30. Alternatively, in the optical module 12, the chromatic aberration correcting lens may be used for both the light projecting lens 21 and the light receiving lens 30.

Further, in the present embodiment, the example of the case has been described where the horizontal color division-type light receiving element 103 for dividing color components of reflected light on the plane is used. However, in the present invention, the configuration of the light receiving element 103 is not restricted to this example. For example, the light receiving element 103 may be a vertical color division-type semiconductor element that is made up of a laminate formed by laminating silicon on the circuit board and divides color components in a depth direction of the silicon layer by use of the fact that optical characteristics of silicon differ by color. In this vertical color division-type light receiving element, photoelectric conversion is performed in accordance with the relation between the wavelength and the depth of light, leading to a small loss in light receiving amount as compared with that in the horizontal color division-type light receiving element.

What is claimed is:

1. A photoelectric switch comprising:
   a surface mount LED mounted on a first surface of a circuit board, configured to generate a light containing a plurality of color components with different hues;
   a light projecting lens configured to concentrate the light generated by the surface mount LED, toward a detection area;
   an optical shield disposed between the surface mount LED and the light projecting lens to shield the light around an optical opening passing the light from the surface mount LED to the light projecting lens;
   a light receiving element configured to selectively receive the light from the detection area in association with a plurality of specific wavelengths, to generate a plurality of light reception signals respectively corresponding to light receiving amounts of the respective specific wavelengths;
   a light receiving lens configured to concentrate the light from the detection area on a light receiving surface of the light receiving element;
   a controller configured to control a light projecting amount of the surface mount LED based on the light reception signals, configured to acquire a receiving color based on the plurality of light reception signals respectively corresponding to the specific wavelengths, configured to compare the receiving color with a reference color to calculate a coincidence degree of both of the receiving color and the reference color, and configured to compare the coincidence degree with a predetermined threshold to generate a detection signal representing a workpiece determination.

2. The photoelectric switch according to claim 1, comprising:
   a platy spacer made of thermally conductive resin, and contacted with a rear surface of the circuit board,
   a metal heat sink plate thermally coupled to the rear surface of the circuit board through the platy spacer, and disposed facing the rear surface of the circuit board; and
   wherein the platy spacer is disposed so as to overlap with the light emitting surface of the light emitting diode projected along a direction perpendicular to the first surface of the circuit board.

3. The photoelectric switch according to claim 2, comprising
   a casing made of a thermally conductive material and configured to accommodate the light emitting diode, the slit, the light projecting lens, the light receiving element, and the light receiving lens; and
   a block-like thermally conductive member made of thermally conductive resin,
   wherein the thermally conductive member is disposed between a side wall of the casing and a bent section of the metal heat sink plate.

4. The photoelectric switch according to claim 3, comprising
   a sheet-like shield member having thermal conductivity and insulating properties, and disposed along the side wall.

5. The photoelectric switch according to claim 3, comprising
   a display unit configured to display the coincidence degree on a display panel provided on the rear surface of the casing.

6. The photoelectric switch according to claim 5, comprising
   a determination threshold specifying unit for specifying the determination threshold based on press operation performed on an operation key provided on the rear surface of the casing,
   wherein the display unit displays the determination threshold on the display panel.

7. The photoelectric switch according to claim 1, comprising
   a light projection spot adjusting unit configured to operate an adjustment screw to adjust a distance to or a size of a light projection spot formed of the detected light.

8. The photoelectric switch according to claim 7, wherein the light projection spot adjusting unit includes:
   a cam plate that has a long hole tilted against a rotation axis direction of the adjustment screw and moves in a direction of the rotation axis in conjunction with rotation of the adjustment screw; and
   a cam slider that has a slider section disposed in the long hole and moves in a direction of a light axis of the light projecting lens in conjunction with movement of the cam plate, and
   the cam slider moves the light projecting lens in the light axis direction by the slider section moving along the inner wall surface of the long hole.

9. The photoelectric switch according to claim 1, wherein at least one of the light projecting lens and the light receiving lens is a chromatic aberration correcting lens, and made up of two or more optical lenses with mutually different dispersion powers.

* * * * *